US00PP08076P

United States Patent [19]

Poor

[11] Patent Number: Plant 8,076

[45] Date of Patent: Dec. 29, 1992

[54] HYBRID TEA ROSE PLANT NAMED SEBAGO

[75] Inventor: Cuyler Poor, Raleigh, N.C.

[73] Assignee: Co-Operative Rose Growers, Inc., Tyler, Tex.

[21] Appl. No.: 694,993

[22] Filed: Apr. 29, 1991

[51] Int. Cl.[5] ..... A01H 5/00

[52] U.S. Cl. ..... Plt./20

[58] Field of Search ..... Plt./11, 20, 21

[56] References Cited

U.S. PATENT DOCUMENTS

P.P. 6,470 12/1988 Suzuki ..... Plt. 20

*Primary Examiner*—Howard J. Locker

*Attorney, Agent, or Firm*—Christie, Parker & Hale

[57] ABSTRACT

A new variety of hybrid tea rose having bright red flowers of good exhibition form.

SUMMARY OF THE INVENTION

The present invention relates to a new and distinct variety of rose plant of the hybrid tea rose class, which was originated by my crossing as seed parent an unnamed and unpatented seedling of my creation and as pollen parent the variety known as 'First Prize ' (U.S. Plant Pat. No. 2,774). The varietal denomination of this new rose is 'Sebago'.

Among the novel characteristics possessed by this new variety which distinguishes it from its parents and all other varieties of which I am aware are its attractive bright red flowers of good exhibition form borne on a plant suitable for growing outdoor in gardens.

Asexual reproduction by propagation by budding of the new variety as performed in Smith Country, Tex. shows that the foregoing and other distinguishing characteristics come true to form and are established and transmitted through succeeding propagations.

1 Drawing Sheet

BRIEF DESCRIPTION OF ILLUSTRATION

The accompanying illustration shows typical specimens of the vegetative growth and flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—Unnamed Seedling.

*Pollen parent.*—'First Prize.'

Class: Hybrid tea.

The following further horticultural observations were made of specimens grown outdoor in Smith County, Tex. in the month of November.

FLOWER

Blooming habit: Continuous.

A. Bud:

(1) *Size.*—Medium.

(2) *Form.*—Ovoid, high centered.

(3) *Color.*—As sepals first divide, near 53B to 46A; after petals begin to unfurl, near 53B.

(4) *Sepals.*—Simple to foliated; longer than bud.

(5) *Peduncle.*—Length — long. Aspect — straight. Strength — erect. Color — near 182B.

B. Bloom:

(1) *Size.*—Average size when fully expanded — about 4¾ inches.

(2) *Borne.*—Singly, one to a stem.

(3) *Form.*—High centered exhibition type with spiral center; outer petals roll under.

(4) *Petalage.*—Number of petals under normal conditions — about 30 to 35.

(5) *Color.*—After sepals fall and petals unfurl, predominant flower color viewing petals' top surface in near 45A, B to 46A, B, C. Color through this range is substantially stable and constant. Petal undersurface is a little lighter, near 46B to C. Pronounced yellow marking near point of petal attached is visible in bud through ⅓ open stage. Petals are near 16B to C toward point of petal attachment. General tonality from a distance is bright red, near 46C, but tends to darkern as flowers age.

C. Petals:

(1) *Texture.*—Thick.

(2) *Appearance.*—Inside velvety and outside satiny.

(3) *Form.*—Acuminate.

(4) *Arrangement.*—Regularly arranged, imbricated.

(5) *Petaloids in center.*—Few.

(6) *Persistence.*—Average.

(7) *Fragrance.*—Slight.

(8) *Lasting quality.*—Average to long lasting on plant and as cut flower.

REPRODUCTIVE ORGANS

A. Stamens, filaments and anthers:

*Arrangement.*—Regularly arranged around styles.

*Color.*—Yellow/orange/red.

B. Pollen:
*Color.*—Gold yellow.
C. Styles: Even, medium length.
D. Stigmas: Full, cream colored.
E. Hips: Globular, medium size, orange/yellow color, seeds protrude slightly.

PLANT

A. Form: Upright, vertical.
B. Growth: Vigorous, uniform branching.
*Height attained.*—About 5 feet.
C. Foliage: Compound 3 and 5 leaflets.
(1) *Size.*—Medium.
(2) *Quantity.*—Abundant.
(3) *Color.*—New foliage: Upper side — purplish green. Under side — near 143B. Old foliage: Upper side — near 137A. Under side — near 183A.
(4) *Shape.*—Ovoid.
(5) *Texture.*—Upper side is leathery, semi-glossy; under side is matte.
(6) *Edge.*—Serrate.
(7) *Serration.*—Ordinary, acuminate apices.

(8) *Leaf stem.*—Color — near 148B with near 143B underside.
(9) *Stipules.*—Medium.
(10) *Resistance to disease.*—Blackspot — Average to good. Mildew — Above average.
D. Wood:
(1) *New wood.*—Color — light green with purplish cast. Bark — smooth.
(2) *Old wood.*—Color — dark green. Bark — smooth.
E. Thorns:
*Quantity (main stalk).*—Ordinary.
*On laterals from stalk.*—Few.
*Form.*—Flat base.
*Length.*—Medium.
*Color.*—Purple when young.
*Position.*—Irregular.
*Prickles.*—Few on main stalks and laterals.
F. Winter hardiness: Above average but needs protection in severe climates.

I claim:

1. A new and distinct variety of rose plant of the hybrid tea rose class, substantially as shown and described.

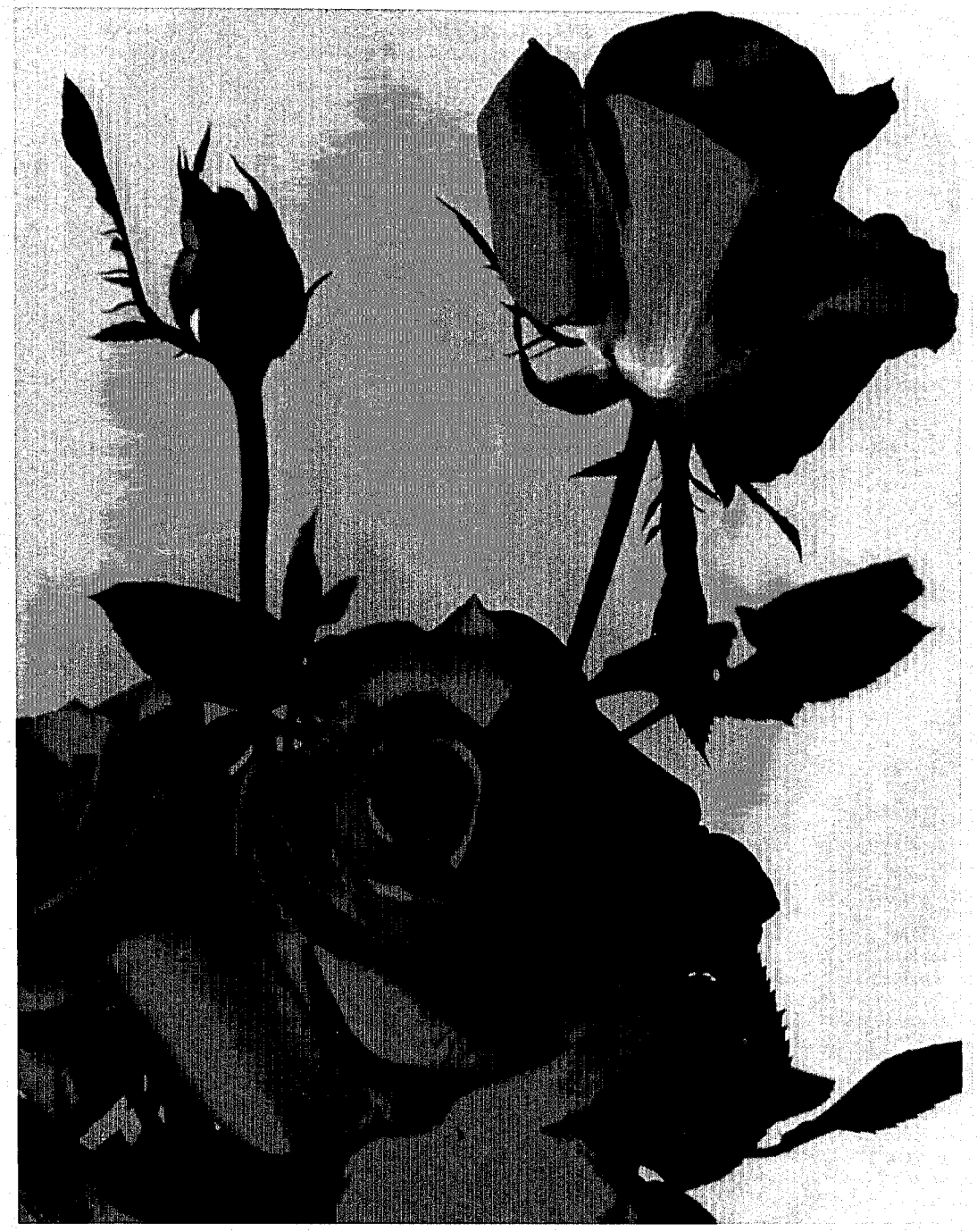

* * * * *